United States Patent [19]

Hagan et al.

[11] Patent Number: 5,547,964

[45] Date of Patent: *Aug. 20, 1996

[54] MEDICAL USE FOR TACHYKININ ANTAGONISTS

[75] Inventors: Russell M. Hagan, Ware, Great Britain; Keith T. Bunce, Research Triangle Park, N.C.

[73] Assignee: Glaxo Group Limited, London, England

[*] Notice: The term of this patent shall not extend beyond the expiration date of Pat. No. 5,360,820.

[21] Appl. No.: 214,306

[22] Filed: Mar. 17, 1994

[30] Foreign Application Priority Data

Mar. 19, 1993 [GB] United Kingdom .................. 9305718

[51] Int. Cl.$^6$ ................................................ A61K 31/445
[52] U.S. Cl. ............................................ 514/329; 514/872
[58] Field of Search ........................................ 514/329, 872

[56] References Cited

U.S. PATENT DOCUMENTS

| | | | |
|---|---|---|---|
| 4,031,226 | 6/1977 | Soudijn | 424/267 |
| 4,066,772 | 1/1978 | Vandenberk | 424/267 |
| 5,102,667 | 4/1992 | Dubroeucq et al. | 424/489 |

FOREIGN PATENT DOCUMENTS

| | | |
|---|---|---|
| 1123088 | 8/1988 | Australia . |
| 0522808 | 1/1993 | European Pat. Off. . |
| 0533280 | 3/1993 | European Pat. Off. . |
| 0627221 | 12/1994 | European Pat. Off. . |
| WO92/17449 | 10/1992 | WIPO . |
| WO93/00331 | 1/1993 | WIPO . |
| WO93/01170 | 1/1993 | WIPO . |

OTHER PUBLICATIONS

Tattersall et al., *European Journal of Pharmacology*, 250, No. 1, Nov. 1993, pp. R5–R6.
Bountra et al., *European Journal of Pharmacology*, 249, No. 1, Nov. 1993, pp. R3–R4.
Niel, *Archives Internationales de Physiologie, de Biochimie et de Biophysique*, 99, No. 5, 1991, pp. A65–A76.
Newton et al., *J. Comp. Neurol.*, 234, 87–104, 1985.
Lesley, *Neurochem. Int.*, 7, 191–211, 1985.
Andrews et al., *TIPS*, 9, 334–341, 1988.
Carpenter et al., *Cell. and Mol. Neurobiol.*, 3, 113–126, 1983.
Carpenter et al., *Fed. Prod. Am. Soc. Exp. Biol.*, 43, 2952–2954, 1984.
Saffroy et al., *Peptides*, 9, 227–241, 1988.

Primary Examiner—Kimberly Jordan
Attorney, Agent, or Firm—Bacon & Thomas

[57] ABSTRACT

The present invention relates to the use of certain tachykinin antagonists, including substance P antagonists and other neurokinin antagonists, in the treatment of emesis.

13 Claims, No Drawings

MEDICAL USE FOR TACHYKININ ANTAGONISTS

The present invention relates to the use of certain tachykinin antagonists, including substance P antagonists and other neurokinin antagonists, in the treatment of emesis.

Tachykinin antagonists are known to be useful in the treatment of a variety of disorders including pain, inflammatory diseases, allergic disorders, CNS disorders, skin disorders, cough and gastrointestinal disorders such as ulcerative colitis and Crohn's disease.

It has now been found that tachykinin antagonists, including substance P antagonists and other neurokinin antagonists, are useful in the treatment of emesis. Our co-pending European Patent Application No. 92202831 (Publication No. 0533280) relates to the use of tachykinin antagonists in the treatment of emesis.

The use of the tachykinin antagonists, including substance P antagonists and other neurokinin antagonists, specifically disclosed in co-pending European Patent Application No. 92202831 in the treatment of emesis is not included within the scope of the present invention.

The invention accordingly provides, in a first aspect, the novel use of the tachykinin antagonists, including substance P antagonists and other neurokinin antagonists, generically and specifically disclosed in published European Patent Application Nos. 512901, 512902, 514273, 514275, 517589, 520555, 522808, 528495, 532456 and published PCT Patent Application Nos. 92/15585, 92/17449, 92/20661, 92/20676, 92/21677, 92/22569, 93/00331, 93/01159, 93/01160, 93/01165, 93/01169 and 93/01170, which disclosures are incorporated herein by reference, in the treatment of emesis.

There is also provided as a further aspect of the invention the use of the tachykinin antagonists, including substance P antagonists and other neurokinin antagonists, generically and specifically disclosed in the above referenced patent specifications in the preparation of a medicament for use in the treatment of emesis.

In an alternative or further aspect there is provided a method for the treatment of a mammal, including man, suffering from or susceptible to emesis, comprising administration of an effective amount of a tachykinin antagonist, including substance P antagonists and other neurokinin antagonists, generically or specifically disclosed in the above referenced patent specifications.

It will be appreciated that reference to treatment is intended to include prophylaxis as well as the alleviation of established symptoms.

Tachykinin antagonists, including substance P antagonists and other neurokinin antagonists, disclosed in the above referenced patent specifications have been shown to have anti-emetic activity as indicated by for example their ability to inhibit cisplatin- or radiation-induced emesis in the ferret.

The treatment of emesis mentioned hereinbefore includes the treatment of nausea, retching and vomiting. Emesis includes acute emesis, delayed emesis and anticipatory emesis. Tachykinin antagonists, including substance P antagonists and other neurokinin antagonists, are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis; pregnancy; vestibular disorders, such as motion sickness and vertigo; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); and opioid analgesics, such as morphine.

Tachykinin antagonists acting at $NK_1$ receptors have been found to be particularly useful in the treatment of emesis.

In a preferred aspect therefore the invention provides the use of an $NK_1$ receptor antagonist generically or specifically disclosed in the above referenced patent specifications in the treatment of emesis.

Particularly preferred tachykinin antagonists for use in the present invention include those generically and specifically disclosed in:

EP512901, i.e. compounds of the formula $$Y\underset{}{\overset{}{\diagup\diagdown}}{}^{(b)}N-(CH_2)_m-C\underset{(CH_2)_p}{\overset{(CH_2)_n}{\diagup\diagdown}}\overset{Q}{\diagdown}N-T-(CH_2)_q-Z \quad (A)$$
$$\qquad\qquad\qquad\qquad\qquad Ar^1$$

wherein

Y represents a group Cy—N or Cy—$CH_2$—N wherein
  Cy represents phenyl optionally substituted by one or more groups, which may be the same or different, selected from halogen, hydroxy, $C_{1-4}$alkoxy, $C_{1-4}$alkyl, trifluoromethyl; $C_{3-7}$cycloalkyl; pyrimidinyl; or pyridyl;

or Y represents a group Ar—$(CH_2)_x$C(X)— wherein
  Ar represents phenyl optionally substituted by one or more groups, which may be the same or different, selected from hydrogen, halogen, hydroxy, $C_{1-4}$alkoxy, trifluoromethyl, $C_{1-4}$alkyl; pyridyl; or thienyl;

x is zero or 1;

X represents hydrogen, hydroxy, $C_{1-4}$alkoxy, $C_{1-4}$acyloxy, carboxy, $C_{1-4}$alkoxycarbonyl, cyano, a group $N(X_1)_2$ wherein $X_1$ represents independently hydrogen, $C_{1-4}$alkyl, hydroxy $C_{1-4}$alkyl, $C_{1-4}$acyl or —$(X_1)_2$ represents, together with the nitrogen atom to which it is attached, a heterocycle selected from pyrrolidine, piperidine or morpholine; a group —S—$X_2$ wherein $X_2$ represents hydrogen or $C_{1-4}$alkyl; or X forms a double bond with an adjacent carbon atom;

m is 2 or 3;

$Ar^1$ represents phenyl optionally substituted by one or more groups, which may be the same or different, selected from halogen, preferably chlorine or fluorine, trifluoromethyl, $C_{1-4}$alkoxy, $C_{1-4}$alkyl; thienyl; benzothienyl; naphthyl; or indolyl;

n is zero 1, 2 or 3;

p is 1 or 2 provided that p is 2 when n is 1 and Q represents two hydrogen atoms;

Q represents oxygen or two hydrogen atoms;

T represents a group selected from C(O) and —$CH_2$—;

q is zero, 1, 2 or 3;

Z represents phenyl optionally substituted by one or more groups selected from halogen, more particularly chlorine or fluorine, trifluoromethyl, $C_{1-4}$alkyl, hydroxyl, $C_{1-4}$alkoxy; naphthyl optionally substituted by one or more groups selected from halogen, trifluoromethyl, $C_{1-4}$alkyl, hydroxyl; pyridyl; thienyl; indolyl; quinolyl; benzothienyl; imidazolyl; or in addition when T represents C(O), —(CH$_2$)$_q$—Z may also represent a benzyl group substituted on the —CH— by hydroxy, $C_{1-4}$alkoxy or $C_{1-4}$alkyl group and optionally substituted on the aromatic ring by halogen, more particularly chlorine or fluorine, trifluoromethyl, $C_{1-4}$alkyl, hydroxy, $C_{1-4}$alkoxy; or an optionally substituted mono-, bi- or tricyclic aromatic or heteroaromatic group; and salts thereof with mineral or organic acids, or, where Y represents Ar—(CH$_2$)$_x$—C(X)—, quarternary ammonium salts or N-oxides formed with the piperidine nitrogen atom (b). EP 512902, i.e. compounds of the formula

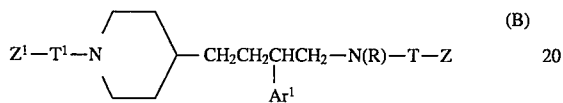

wherein

Ar$^1$ represents phenyl optionally substituted by halogen, $C_{1-3}$alkyl, trifluoromethyl, $C_{1-3}$alkoxy or hydroxy; thienyl, pyridyl or naphthyl optionally substituted by halogen; indolyl; or benzothienyl;

R represents hydrogen, methyl or (CH$_2$)$_n$L;

n represents 2 to 6;

L represents hydrogen or amino;

Z and Z$^1$ represent hydrogen, M or OM;

M represents hydrogen, $C_{1-6}$alkyl, a-hydroxybenzyl, a-($C_{1-3}$alkyl)benzyl, phenyl$C_{1-3}$alkyl (optionally ring substituted by halogen, hydroxy, $C_{1-4}$alkoxy or $C_{1-4}$alkyl), pyridyl$C_{1-3}$alkyl, naphthyl$C_{1-3}$alkyl, pyridylthio$C_{1-3}$alkyl, styryl, 1-methyl-2-imidiazolylthio$C_{1-3}$alkyl, 1-oxo-3-phenyl-2-indanyl, or optionally substituted aryl or heteroaryl;

T$^1$=a bond, CH$_2$ or CO;

T=CO or C(W)NH;

W=O or S;

with the proviso that (a) T$^1$ is not a bond when Z$^1$ is hydrogen or OM; and (b) T is not C(W)NH when Z is hydrogen or OM;

and acid addition and quarternary ammonium salts thereof.

EP 514273, i.e. compounds of the formula

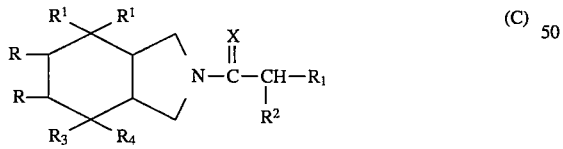

wherein

R each represent hydrogen or together form a bond;

R$^1$ are the same and represent phenyl optionally substituted in the 2- or 3-position by halogen or methyl;

X represents O or NH;

R$_1$ represents phenyl optionally substituted by one or more halogen, hydroxy, alkyl (optionally substituted by halogen, amino, alkylamino or dialkylamino), alkyloxy or alkylthio (both optionally substituted by hydroxy, amino, alkylamino, dialkylamino (optionally substituted by phenyl, hydroxy or amino) or dialkylamino where the alkyl groups form, together with the nitrogen atom to which they are attached, a 5- or 6-membered heterocyclic ring which may contain a further heteroatom selected from oxygen, sulfur or nitrogen, optionally substituted by alkyl, hydroxy or hydroxyalkyl), or substituted by amino, alkylamino, dialkylamino (where the alkyl groups, together with the nitrogen atom to which they are attached, may form a heterocycle as defined above), or R$_1$ represents cyclohexadienyl, naphthyl, or a 5–9-membered mono- or polyheterocyclic ring, optionally saturated, and containing one more heteroatoms selected from oxygen, nitrogen and sulfur;

R$_2$ represents hydrogen, halogen, hydroxy, alkyl, aminoalkyl, alkylaminoalkyl, dialkylaminoalkyl, alkyloxy, alkylthio, acyloxy, carboxy, alkyloxycarbonyl, dialkylaminoalkyloxycarbonyl, benzyloxycarbonyl, amino, acylamino, or alkyloxycarbonylamino;

R$_3$ represents halogen or hydroxy;

R$_4$ represents hydrogen; or R$_3$ and R$_4$ are both halogen; and salts thereof.

EP 514275; i.e. compounds of the formula

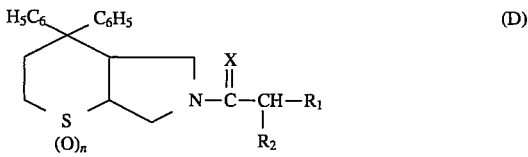

wherein X represents NH or an oxygen atom;

R$_1$ represents phenyl optionally substituted by one or more groups selected from halogen, hydroxy, alkyl (optionally substituted by halogen, amino, alkylamino or dialkylamino), alkyloxy or alkylthio [optionally substituted by hydroxy, amino, alkylamino or dialkylamino (optionally substituted by phenyl, hydroxy or amino), or dialkylamino where the alkyl groups form, together with the nitrogen atom to which they are attached, a 5- or 6-membered heterocyclic ring optionally containing a further heteroatom selected from oxygen, sulphur or nitrogen, optionally substituted by alkyl, hydroxy or hydroxyalkyl], or substituted by amino, alkylamino, dialkylamino where the alkyl groups optionally form, together with the nitrogen atom to which they are attached, a heterocycle as defined above, or represent a cyclohexadienyl, naphthyl or a mono or polycylic, saturated or unsaturated, ring containing 5 to 9 carbon atoms and one or more heteroatoms selected from oxygen, nitrogen or sulphur;

R$_2$ represents hydrogen, halogen, hydroxy, alkyl, aminoalkyl, alkylaminoalkyl, dialkylaminoalkyl, alkyloxy, alkylthio, acyloxy, carboxy, alkyloxycarbonyl, dialkylaminoalkyloxycarbonyl, benzyloxycarbonyl, amino, alkylamino or alkyloxycarbonylamino; n is an integer from zero to 2; and salts thereof.

EP 520555, i.e. compounds of the formula (E) or a salt or prodrug thereof

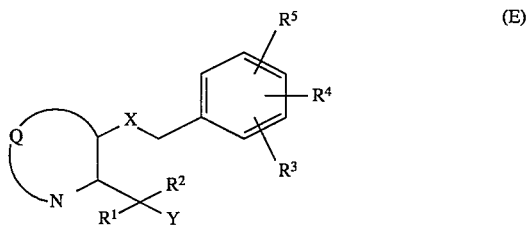

wherein

Q is the residue of an optionally substituted azabicyclic ring system;

X represents oxa or thia;

Y represents H or hydroxy;

$R^1$ represents phenyl or thienyl, either of which groups may be optionally substituted by halo, trifluoromethyl or $C_{1-3}$ alkoxy, or $C_{5-7}$ cycloalkyl;

$R^2$ represents benzyl which may be substituted in the benzyl ring by halo, trifluoromethyl or $C_{1-3}$ alkoxy, or $C_{5-7}$ cycloalkyl; and $R^3$, $R^4$ and $R^5$ independently represent H, $C_{1-6}$ alkyl, $C_{2-6}$ alkenyl, $C_{2-6}$ alkynyl, halo, cyano, nitro, trifluoromethyl, trimethylsilyl, —$OR^a$, $SCH_3$, $SOCH_3$, $SO_2CH_3$, —$NR^aR^b$, —$NR^aCO_2R^b$, —$NR^aCO_2R^b$, —$CO_2R^a$ or —$CONR^aR^b$; and $R^a$ and $R^b$ independently represent H, $C_{1-6}$ alkyl, phenyl or trifluoromethyl.

EP 522808, i.e compounds of formula (F) or a salt or prodrug thereof

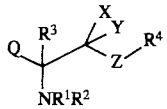
(F)

wherein

Q represents $R^9CR^{10}R^{11}$ or $CH_2R^9CR^{10}R^{11}$ where $R^9$ is H or hydroxy and $R^{10}$ and $R^{11}$ each independently represent optionally substituted phenyl, optionally substituted benzyl, $C_{5-7}$ cycloalkyl or ($C_{5-7}$ cycloalkyl)methyl;

$R^1$ and $R^2$ independently represent H; $C_{1-6}$ alkyl optionally substituted by hydroxy, cyano, $COR^a$, $COOR^a$, $CONR^aR^b$, $COC_{1-6}alkylNR^aR^b$, $CONR^{12}C_{1-6}alkylOR^a$, $CONR^{12}C_{1-6}alkylCONR^aR^b$ or $NR^aR^b$ (where $R^a$ and $R^b$ each independently represent H, $C_{1-6}$alkyl, phenyl (optionally substituted by one or more of $C_{1-6}$alkyl, $C_{1-6}$alkoxy, halo and trifluoromethyl), phenyl($C_{1-4}$alkyl) (optionally substituted in the phenyl ring by one or more of $C_{1-6}$alkyl, $C_{1-6}$alkoxy, halo and trifluoromethyl) or $R^a$ and $R^b$ together form a chain $(CH_2)_p$ optionally substituted by oxo where p is 4 or 5 and where one methylene group may optionally be replaced by an oxygen atom or a group $NR^x$, where $R^x$ is H or $C_{1-6}$alkyl, and $R^{12}$ represents H, $C_{1-6}$alkyl, phenyl (optionally substituted by one or more of $C_{1-6}$alkyl, $C_{1-6}$alkoxy, halo and trifluoromethyl) or phenyl ($C_{1-4}$alkyl) (optionally substituted in the phenyl ring by one or more of $C_{1-6}$alkyl, $C_{1-6}$alkoxy, halo and trifluoromethyl); phenyl($C_{1-4}$alkyl) (optionally substituted by one or more of $C_{1-6}$alkyl, $C_{1-6}$alkoxy, halo and trifluoromethyl in the phenyl ring); $C_{2-6}$alkenyl; $C_{2-6}$alkynyl; $COR^a$; $COOR^a$, $COC_{1-6}alkylhalo$; $COC_{1-6}alkylNR^aR^b$; $CONR^{12}C_{1-6}alkylCONR^aR^b$; $CONR^aR^b$ or $SO_2R^a$; (where $R^a$, $R^b$ and $R^{12}$ are as previously defined) or $R^1$ and $R^2$ together form a chain $(CH_2)_q$ optionally substituted by oxo where q is 4 or 5 and where one methylene group may optionally be replaced by an oxygen atom or a group $NR^x$, where $R^x$ is H or $C_{1-6}$alkyl;

$R^3$ represents H, $C_{1-6}$alkyl or $C_{2-6}$alkenyl;

$R^4$ represents $C_{1-3}$alkyl substituted by a phenyl group which may itself optionally be substituted by one or more of $C_{1-6}$alkyl, $C_{2-6}$alkenyl, $C_{2-6}$alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ and $CONR^cR^d$, where $R^c$ and $R^d$ independently represent H, $C_{1-6}$alkyl, phenyl or trifluoromethyl;

X and Y each represent H, or X and Y together represent a group =O; and

Z represents O, S or $NR^7$, where $R^7$ represents H or $C_{1-6}$alkyl; with the exception of DL-diphenylalanine benzyl ester;

2-benzamido-3,3-diphenylpropanoyl benzamide; and 2-benzamido-3,4-diphenyl-butanoyl benzamide.

For example 2-ammonium-1-((3,5-bis(trifluoromethyl)phenyl)methyloxy)-3,3-diphenylpropane—Compound 1; and salts and prodrugs thereof.

EP 528495, i.e. compounds of formula (G) or a salt or prodrug thereof

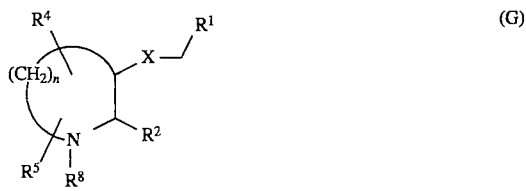
(G)

wherein n is 1, 2, or 3 and where any carbon atom of $(CH_2)_n$ may be substituted by $R^4$ and/or $R^5$;

X represents O or S;

$R^1$ represents phenyl optionally substituted by 1, 2 or 3 groups selected from $C_{1-6}$alkyl, $C_{2-6}$alkenyl; $C_{2-6}$alkynyl, halo, cyano, nitro, trifluoromethyl, trimethylsilyl, —$OR^a$, $SR^a$, $SOR^a$, $SO_2R^a$, —$NR^aR^b$, —$NR^aCOR^b$, —$NR^aCO_2R^b$, $CO_2R^a$ or —$CONR^aR^b$;

$R^2$ represents aryl selected from phenyl and naphthyl; heteroaryl selected from indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, halo or trifluoromethyl;

$R^4$ and $R^5$ each independently represent H, halo, $CH_2OR^9$, $C_{1-6}$alkyl, oxo, $CO_2R^{10}$ or $CONR^{10}R^{11}$;

$R^8$ represents H, $COR^9$, $CO_2R^{10}$, $COCONR^{10}R^{11}$, $COCO_2R^{10}$ or $C_{1-6}$alkyl optionally substituted by a group selected from ($CO_2R^{10}$, $CONR^{10}R^{11}$, hydroxy, cyano, $COR^9$, $NR^{10}R^{11}$, $C(NOH)NR^{10}R^{11}$, $CONHphenyl-(C_{1-4}alkyl)$, $COCO_2R^{10}$, $COCONR^{10}R^{11}$ and phenyl optionally substituted by one or more substituents selected from $C_{1-6}$alkyl, $C_{1-6}$alkoxy, halo and trifluoromethyl);

$R^a$ and $R^b$ each independently represent H, $C_{1-6}$alkyl, phenyl or trifluoromethyl;

$R^9$ represents H, $C_{1-6}$alkyl or phenyl; and $R^{10}$ and $R^{11}$ each independently represent H or $C_{1-6}$alkyl.

For example cis-3-((3,5-dimethylphenyl)methyloxy)-2-phenylpiperidine—Compound 5; and salts (e.g. the hydrochloride salt) and prodrugs thereof.

WO 92/22569, i.e. compounds of formula

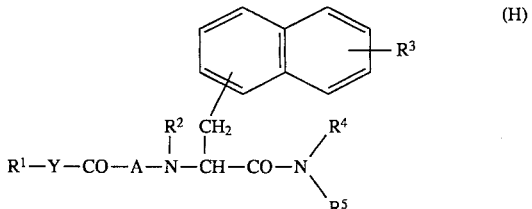
(H)

wherein $R^1$ is lower alkyl, aryl, ar(lower)alkyl, arylamino, pyridyl, pyrrolyl, pyrazolopyridyl, quinolyl, or a group of the formula

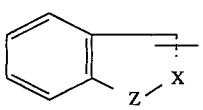

wherein the symbol of a line and dotted line is a single bond or a double bond,

X is CH or N, and

Z is O, S or NH, each of which may have suitable substituent(s);

$R^2$ is hydrogen or lower alkyl;

$R^3$ is hydrogen or suitable substituent;

$R^4$ is lower alkyl which may have suitable substituent(s), and $R^5$ is ar(lower)alkyl which may have suitable substituent(s) or pyridyl(lower)alkyl, or $R^4$ and $R^5$ are linked together to form benzene-condensed lower alkylene;

A is an amino acid residue which may have suitable substituent(s); and

Y is bond, lower alkylene, lower alkenylene or lower alkylimino, provided that when $R^1$ is aryl, or a group of the formula:

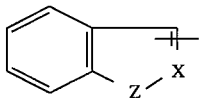

wherein X is as defined above, and

Z is O or N—$R^6{}_a$, in which $R^6{}_a$ is hydrogen or lower alkyl, $R^2$ is hydrogen, $R^4$ is lower alkyl which may have suitable substituent(s), $R^6$ is ar(lower)alkyl which may have suitable substituent(s), A is group of the formula:

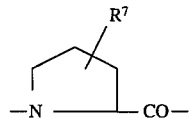

wherein $R^7$ is hydroxy or lower alkoxy, and

Y is bond or lower alkenylene, then $R^3$ is suitable substituent.

WO 92/15585, i.e. compounds of the formula

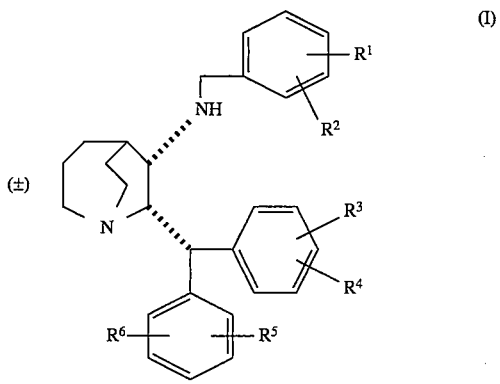

wherein $R^1$, $R^2$, $R^3$, $R^4$, $R^5$, and $R^6$ are each independently selected from hydrogen, fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety, and benzyloxycarbonyl; and the pharmaceutically acceptable salts of such compounds.

WO 92/17449, i.e. compounds of the formula

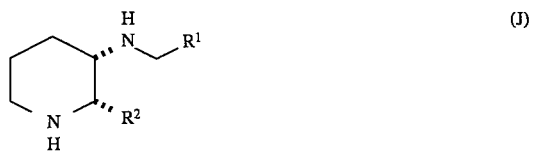

wherein $R^1$ is aryl selected from indanyl, phenyl and naphthyl; heteroaryl selected from thienyl, furyl, pyridyl and quinolyl; and cycloalkyl having 3 to 7 carbon atoms, wherein one of said carbon atoms may optionally be replaced by nitrogen, oxygen or sulfur; wherein each of said aryl and heteroaryl groups may optionally be substituted with one or more substituents, and said ($C_3$–$C_7$)cycloalkyl may optionally be substituted with one or two substituents, said substituents being independently selected from chloro, fluoro, bromo, iodo, nitro, ($C_1$–$C_{10}$)alkyl optionally substituted from one to three fluoro groups, ($C_1$–$C_{10}$)alkoxy optionally substituted with from one to three fluoro groups, amino, ($C_1$–$C_{10}$)alkyl-S—, ($C_1$–$C_{10}$)alkyl-S(O)—, ($C_1$–$C_{10}$)alkyl-$SO_2$—, phenyl, phenoxy, ($C_1$–$C_{10}$)alkyl-$SO_2$NH—, ($C_1$–$C_{10}$)alkyl-$SO_2$NH-($C_1$–$C_{10}$)alkyl-, ($C_1$–$C_{10}$)alkylamino-di($C_1$–$C_{10}$)alkyl-, cyano, hydroxy, cycloalkoxy having 3 to 7 carbon atoms, ($C_1$–$C_6$)alkylamino, ($C_1$–$C_6$)dialkylamino, HC(O)NH— and ($C_1$–$C_{10}$)alkyl-C(O)—NH—, wherein the nitrogen atoms of said amino and ($C_1$–$C_6$)alkylamino groups may optionally be protected with an appropriate protecting group; and $R^2$ is thienyl, benzhydryl, naphthyl or phenyl optionally substituted with from one to three substituents independently selected from chloro, bromo, fluoro, iodo, cycloalkoxy having 3 to 7 carbon atoms, ($C_1$–$C_{10}$)alkyl optionally substituted with from one to three fluoro groups and ($C_1$–$C_{10}$)alkoxy optionally substituted with from one to three fluoro groups.

For example
(2S,3S)-3-(2-Methoxy-5-methylmercaptobenzylamino)-2-phenylpiperidine—Compound 2.

WO 92/20661, i.e. compounds of the formula

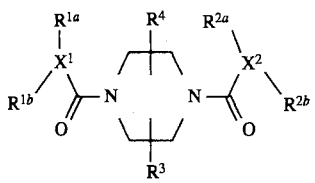

(K)

or a pharmaceutically acceptable salt thereof wherein:
$R^{1a}$ is
1) H,
2) $C_{1-8}$ alkyl,
3) phenyl, either unsubstituted or substituted with one or two substituents selected from:
   a) —$C_{1-4}$ alkyl,
   b) -halo,
   c) —OH,
   d) —$CF_3$,
   e) —$NH_2$,
   f) —NH($C_{1-4}$ alkyl),
   g) —N($C_{1-4}$ alkyl)$_2$,
   h) —$CO_2$H,
   i) —$CO_2$($C_{1-4}$ alkyl), and
   j) —$C_{1-4}$ alkoxy; or
4) $C_{1-4}$ alkyl-phenyl, wherein the phenyl is either unsubstituted or substituted with one or two substituents selected from:
   a) —$C_{1-4}$ alkyl,
   b) -halo,
   c) —OH,
   d) —$CF_3$,
   e) —$NH_2$,
   f) —NH($C_{1-4}$ alkyl),
   g) —N($C_{1-4}$ alkyl)$_2$,
   h) —$CO_2$H,
   i) —$CO_2$($C_{1-4}$ alkyl), and
   j) —$C_{1-4}$ alkoxy;
$R^{1b}$ is
1) $R^{1a}$,
2) —$C_{3-7}$ cycloalkyl, or
3) —$CH_2$—$R^{1a}$;
$R^{2a}$ and $R^{2b}$ are independently phenyl, either unsubstituted or substituted with one or two substituents selected from:
1) —$C_{1-4}$ alkoxy,
2) -halo,
3) —OH,
4) —$CF_3$
5) —$NH_2$,
6) —N($C_{1-4}$ alkyl),
7) —N($C_{1-4}$ alkyl)$_2$,
8) —$CO_2$H,
9) —$CO_2$($C_{1-4}$ alkyl), and
10) —$C_{1-6}$ alkyl, either unsubstituted or substituted with:
    a) -halo,
    b) —OH,
    c) —$CF_3$,
    d) —$NH_2$,
    e) —NH($C_{1-4}$ alkyl),
    f) —N($C_{1-4}$ alkyl)$_2$,
    g) —$CO_2$H,
    h) —$CO_2$($C_{1-4}$ alkyl), and
    i) —$C_{1-4}$ alkoxy,
    j) —S(O)$_x$($C_{1-4}$ alkyl) wherein x is 0, 1 or 2,
    k) —$C_{3-7}$ cycloalkyl;

and the phenyl groups of $R^{2a}$ and $R^{2b}$ may be joined together at the ortho carbon atoms through a carbon-carbon single bond or $C_{1-3}$ alkylene to form a tricyclic group with the $X^2$ to which they are attached;

$X^1$ is —N, —CH or 0, and if $X^1$ is 0, $R^{1a}$ is absent;
$X^2$ is —N or —CH;
$R^3$ is
1) —$C_{1-4}$ alkyl,
2) —$CO_2R^6$,
3) —$CH_2OCOR^6$,
4) —$CH_2OH$,
5) —$CH_2OR^5$,
6) —$CH_2S(O)_xR^5$,
7) —$CH_2OCONR^5R^6$,
8) —$CH_2CONR^5R^6$,
9) $CONR^5R^6$,
10) —$CO_2R^8$,
11) —$CH_2CO_2R^6$,
12) —$CH_2CO_2R^8$,
13) —$CONRSO_2R^9$,
14) —$CH_2N(R^6)CONR^5R^6$,
15) —$CH_2NH_2$,
16) —$CH_2NH(C_{1-4}$ alkyl), or
17) —$CH_2N(C_{1-4}$alkyl)$_2$; wherein $R^5$ is $C_{1-6}$ alkyl either unsubstituted or substituted with:
1) -halo,
2) —OH,
3) —$CF_3$
4) —$NH_2$,
5) —NH($C_{1-4}$ alkyl),
6) —N($C_{1-4}$ alkyl)$_2$,
7) —$CO_2$H,
8) —$CO_2$($C_{1-4}$ alkyl),
9) —$C_{3-7}$ cycloalkyl, or
10) phenyl, either unsubstituted or substituted with
    a) —$C_{1-4}$ alkyl,
    b) -halo,
    c) —OH,
    d) —$CF_3$
    e) —$NH_2$,
    f) —NH($C_{1-4}$ alkyl),
    g) —N($C_{1-4}$ alkyl)$_2$,
    h) —$CO_2$H, or
    i) —$CO_2$($C_{1-4}$ alkyl);
$R^6$ is —H or $C_{1-4}$ alkyl; or
$R^5$ and $R^6$ can be joined together to form with the nitrogen to which they are attached —N(CH$_2$CH$_2$)$_2$L; wherein L is:
i) a single bond,
ii) —OH$_2$—,
iii) —O—,
iv) —S(O)$_p$—, or
v) —NR$^7$;
$R^7$ is
1) —H,
2) —$C_{1-6}$alkyl, unsubstituted or substituted with —OH, —$C_{1-4}$ alkoxy or —N($C_{1-4}$alkyl)$_2$,
3) -aryl, or
4) —$CH_2$-aryl;
$R^8$ is
1) —H,
2) —CH($R^7$)OCOR$^{10}$, wherein R$^{10}$ is
    a) —$C_{1-6}$alkyl,
    b) -aryl, or
    c) —$CH_2$-aryl,
3) —$CH_2$-aryl, $R^9$ is
1) -aryl,
2) -heteroaryl,
3) —$C_{3-7}$cycloalkyl,
4) polyfluoro-$C_{1-4}$ alkyl
5) —$C_{1-6}$alkyl, either unsubstituted or substituted with
   a) -aryl,
   b) -heteroaryl,
   c) OH,
   d) —SH,
   e) —$C_{1-4}$alkyl,
   f) —$C_{3-7}$cycloalkyl,
   g) —$C_{1-4}$alkoxy
   h) —$C_{1-4}$alkylthio,
   i) —$CF_3$,
   j) -halo,
   k) —$NO_2$,
   l) —$CO_2R^6$,
   m) —$N(R^6)_2$, wherein the $R^6$ groups are the same or different,
   n) —NH-aryl,
   o) —$N(aryl)_2$,
   p) —$PO_3H$,
   q) —PO(OH)($OC_{1-4}$alkyl) or
   r) —$N(CH_2CH_2)_2L$ wherein L is as defined above, and $R^4$ is H or $R^3$.

WO 92/20676, i.e. compounds of the formula

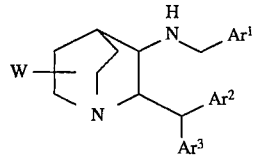

(L)

wherein W is Y or $X(CH_2)_n$;

Y is optionally substituted ($C_1$-$C_6$)alkyl, optionally substituted ($C_2$-$C_6$)alkenyl or optionally substituted ($C_3$-$C_6$)cycloalkyl;

X is optionally substituted ($C_1$-$C_6$)alkoxy, $CONR^1R^2$, $CO_2R^1$, $CHR^1OR^2$, $CHR^1NR^2R^3$, $COR^1$, $CONR^1OR^2$ or optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl; and n is an integer from zero to six;

$Ar^1$, $Ar^2$ and $Ar^3$ are each, independently, optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl; and $R^1$, $R^2$ and $R^3$ are independently selected from hydrogen, optionally substituted ($C_1$-$C_6$)alkyl, optionally substituted ($C_1$-$C_6$)alkoxy, optionally substituted ($C_3$-$C_8$)cycloalkyl, optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl; and optionally substituted ($C_1$-$C_5$)heterocyclic groups, wherein said heterocyclic groups are selected from pyrrolidino, piperidino, morpholino, piperazinyl and thiamorpholino;

and wherein the substituents on the foregoing substituted alkyl, alkenyl, cycloalkyl and alkoxy groups are independently selected from halo, nitro, amino, ($C_1$-$C_4$)alkyl, ($C_1$-$C_4$)alkoxy, trifluoromethyl and trifluoromethoxy;

and wherein the substituents on the foregoing substituted heterocyclic groups are attached to an oxygen or nitrogen atom on the ring and are independently selected from oxygen and ($C_1$-$C_4$)alkyl;

and wherein the substituents on said substituted $Ar^1$ groups are independently selected from ($C_1$-$C_6$)alkyl optionally substituted with from one to three halo groups. ($C_1$-$C_6$)alkoxy optionally substituted from one to three halo groups, ($C_1$-$C_6$)alkylsulfinyl, ($C_2$-$C_6$)alkenyl, ($C_1$-$C_6$)alkylthio, ($C_1$-$C_6$)alkylsulfonyl, ($C_1$-$C_6$)alkylsulfonylamino, and di-($C_1$-$C_6$)alkylamino wherein one or both of the alkyl groups may be optionally substituted with a ($C_1$-$C_6$)alkylsulfonyl, or ($C_1$-$C_6$)alkylsulfinyl group;

and wherein the substituents on said substituted $Ar^2$ and $Ar^3$ groups are independently selected from ($C_1$-$C_4$)alkyl, ($C_1$-$C_4$)alkoxy, ($C_1$-$C_4$)alkylthio, ($C_1$-$C_4$)alkylsulfinyl, di-($C_1$-$C_4$)alkylamino, trifluoromethyl and trifluoromethoxy, and wherein the substituents on said substituted ($C_1$-$C_5$) heterocyclic groups are independently selected from oxygen and ($C_1$-$C_4$)alkyl.

WO 92/21677, i.e. compounds of the formula

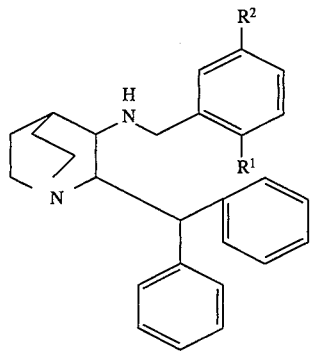

(M)

wherein $R^1$ is methoxy and $R^2$ is independently selected from the group consisting of isopropyl, tert-butyl, methyl, ethyl and sec-butyl; and the pharmaceutically acceptable salts of such compounds.

WO 93/00331, i.e. compounds of the formula

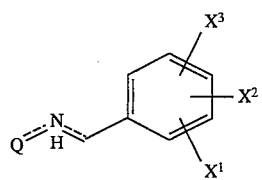

(N)

wherein $X^1$ is hydrogen, ($C_1$-$C_{10}$)alkoxy optionally substituted with from one to three fluorine atoms or ($C_1$-$C_{10}$)alkyl optionally substituted with from one to three fluorine atoms;

$X^2$ and $X^3$ are independently selected from hydrogen, halo, nitro, ($C_1$-$C_{10}$)alkyl optionally substituted with from one to three fluorine atoms, ($C_1$-$C_{10}$)alkoxy optionally substituted with from one to three fluorine atoms, trifluoromethyl, hydroxy, phenyl, cyano, amino, ($C_1$-$C_6$)-alkylamino, di-($C_1$-$C_6$)alkylamino, —C(O)—NH-($C_1$-$C_6$)-alkyl, ($C_1$-$C_6$)alkyl-C(O)—NH-($C_1$-$C_6$)alkyl, hydroxy($C_1$-$C_4$)alkyl, ($C_1$-$C_4$)alkoxy($C_1$-$C_4$)alkyl, —NHC(O)H and —NHC(O)-($C_1$-$C_6$)alkyl; and Q is a group of the formula

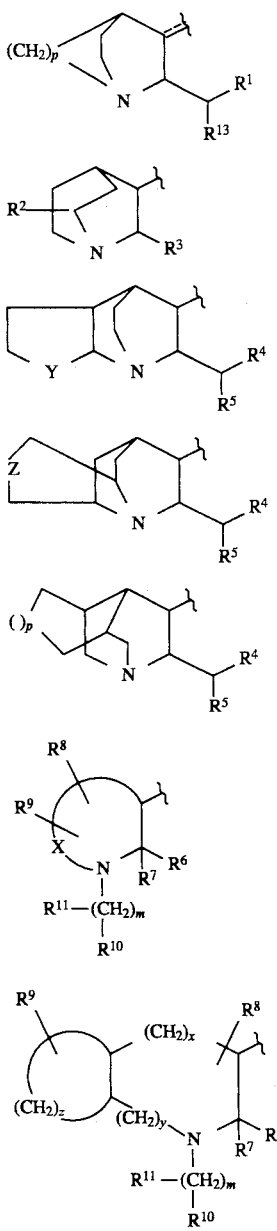

II

III

IV

V

VI

VII

VIII wherein $R^1$ is a radical selected from furyl, thienyl, pyridyl, indolyl, biphenyl and phenyl optionally substituted with one or two substituents independently selected from halo, $(C_1-C_{10})$alkyl optionally substituted with from one to three fluorine atoms, $(C_1-C_{10})$alkoxy optionally substituted with from one to three fluorine atoms, carboxy, benzyloxycarbonyl and $(C_1-C_3)$alkoxy-carbonyl;

$R^{13}$ is selected from $(C_3-C_4)$ branched alkyl, $(C_5-C_6)$ branched alkenyl, $(C_5-C_7)$cycloalkyl, and the radicals named in the definition of $R^1$;

$R^2$ is hydrogen or $(C_1-C_6)$alkyl;

$R^3$ is phenyl, biphenyl, naphthyl, pyridyl, benzhydryl, thienyl or furyl, and $R^3$ may optionally be substituted with from one to three substituents independently selected from halo, $(C_1-C_{10})$alkyl optionally substituted with from one to three fluorine atoms and $(C_1-C_{10})$alkoxy optionally substituted with from one to three fluorine atoms;

Y is $(CH_2)_l$ wherein l is an integer from one to three or Y is a group of the formula Z is oxygen, sulfur, amino, $(C_1-C_3)$alkylamino or $(CH_2)_n$ wherein n is zero, one or two;

o is two or three;

p is zero or one;

$R^4$ is furyl, thienyl, pyridyl, indolyl, biphenyl, or phenyl optionally substituted with one or two substituents independently selected from halo, $(C_1-C_{10})$alkyl optionally substituted with from one to three fluorine atoms, $(C_1-C_{10})$alkoxy optionally substituted with from one to three fluorine atoms, carboxy, $(C_1-C_3)$alkoxy-carbonyl and benzyloxycarbonyl;

$R^5$ is thienyl, biphenyl or phenyl optionally substituted with one or two substituents independently selected from halo, $(C_1-C_{10})$alkyl optionally substituted with from one to three fluorine atoms and $(C_1-C_{10})$alkoxy optionally substituted with from one to three fluorine atoms;

each of the two dashed lines in formula (N) and the dashed line in formula (II) represent an optional double bond that may optionally exist when Q is a group of the formula (II);

X is $(CH_2)_q$ wherein q is an integer from 1 to 6, and wherein any one of the carbon-carbon single bonds in said $(CH_2)_q$ may optionally be replaced by a carbon-carbon double bond, and wherein any one of the carbon atoms of said $(CH_2)_q$ may optionally be substituted with $R^8$, and wherein any one of the carbon atoms of said $(CH_2)_q$ may optionally be substituted with $R^9$;

m is an integer from 0 to 8, and any one of the carbon-carbon single bonds of $(CH_2)_m$ may optionally be replaced by a carbon-carbon double bond or a carbon-carbon triple bond, and any one of the carbon atoms of said $(CH_2)_m$ may optionally be substituted with $R^{11}$;

$R^6$ is a radical selected from hydrogen, $(C_1-C_6)$ straight or branched alkyl, $(C_3-C_7)$cycloalkyl wherein one of the carbon atoms may optionally be replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl $(C_2-C_6)$alkyl, benzhydryl and benzyl, wherein each of said aryl and heteroaryl groups and the phenyl moieties of said benzyl, phenyl $(C_2-C_6)$alkyl and benzhydryl may optionally be substituted with one or more substituents independently selected from halo, nitro, $(C_1-C_{10})$alkyl optionally substituted with from one to three fluorine atoms, $(C_1-C_{10})$alkoxy optionally substituted with from one to three fluorine atoms, amino, hydroxy-$(C_1-C_6)$alkyl, $(C_1-C_6)$alkoxy-$(C_1-C_6)$alkyl, $(C_1-C_6)$-alkylamino, $(C_1-C_6)$alkyl-O—C(O)—, $(C_1-C_6)$alkyl—O—C(O)—C-$(C_1-C_6)$alkyl, $(C_1-C_6)$alkyl-C(O)—(O)—, $(C_1-C_6)$alkyl-C(O)-$(C_1-C_6)$alkyl-O—, $(C_1-C_6)$alkyl-C—(O), $C_1-C_6)$alkyl-C(O)-$(C_1-C_6)$alkyl-, di-$(C_1-C_6)$alkylamino, —C(O)NH-$(C_1-C_6)$-alkyl-, $(C_1-C_6)$alkyl-C(O)—NH-$(C_1-C_6)$alkyl, —NHC(O)H and —NHC(O)-$(C_1-C_6)$alkyl; and wherein one of the phenyl moieties of said benzhydryl may optionally be replaced by naphthyl, thienyl, furyl or pyridyl;

$R^7$ is hydrogen, phenyl or $(C_1-C_6)$alkyl;

or $R^6$ and $R^7$, together with the carbon to which they are attached, form a saturated carbocyclic ring having from 3 to 7 carbon atoms wherein one of said carbon atoms may optionally be replaced by oxygen, nitrogen or sulfur;

$R^8$ and $R^9$ are each independently selected from hydrogen, hydroxy, halo, amino, oxo (=O), nitrile, hydroxy-$(C_1-C_6)$alkyl, $(C_1-C_6)$alkoxy-$(C_1-C_6)$alkyl, $(C_1-C_6)$alkylamino, di-$(C_1-C_6)$alkylamino, $(C_1-C_6)$alkoxy, $(C_1-C_6)$alkyl-O—C(O)—, $(C_1-C_6)$alkyl-O—C(O)-$(C_1-C_6)$alkyl, $(C_1-C_6)$alkyl-C(O)—O, $(C_1-C_6)$alkyl-C(O)$(C_1-C_6)$alkyl-O—, $(C_1-C_6)$alkyl-C(O)—, $(C_1-C_6)$alkyl-C(O)$(C_1-C_6)$alkyl-, and the radicals set forth in the definition of $R^6$;

$R^{10}$ is $NHCR^{12}$, $NHCH_2R^{12}$, $NHSO_2R^{12}$ or one of the radicals set forth in any of the definitions of $R^6$, $R^8$ and $R^9$;

$R^{11}$ is oximino (=NOH) or one of the radicals set forth in any of the definitions of $R^6$, $R^8$ and $R^9$; and $R^{12}$ is $(C_1-C_6)$alkyl, hydrogen, or phenyl$(C_1-C_6)$alkyl or optionally substituted with $(C_1-C_6)$alkyl; and with the proviso that (a) when m is 0, $R^{11}$ is absent, (b) neither $R^8$, $R^9$, $R^{10}$ nor $R^{11}$ can form, together with the carbon to which it is attached, a ring with $R^7$, (c) when Q is a group of the formula VIII, $R^8$ and $R^9$ cannot be attached to the same carbon atom, (d) when $R^8$ and $R^9$ are attached to the same carbon atom, then either each of $R^8$ and $R^9$ is independently selected from hydrogen, fluoro, $(C_1-C_6)$alkyl, hydroxy-$(C_1-C_6)$alkyl and $(C_1-C_6)$alkoxy-$(C_1-C_6)$alkyl, or $R^8$ and $R^9$, together with the carbon to which they are attached, form a $(C_3-C_6)$ saturated carbocyclic ring that forms a spiro compound with the nitrogen-containing ring to which they are attached, (e) the nitrogen of formula (N) can not be double bonded to both Q and the substituted benzyl group to which it is attached, (f) when Q is a group of the formula VII and q is 2 and either $R^8$ or $R^9$ is 5-hydroxy-$(C_1-C_6)$alkyl or 5-$(C_1-C_6)$alkoxy-$(C_1-C_6)$alkyl, then the other of $R^8$ and $R^9$ is either 5-$(C_1-C_6)$alkyl or hydrogen; (g) when Q is a group of the formula VII and q is 2, then neither $R^8$ nor $R^9$ is 4-hydroxy-$(C_1-C_6)$alkyl or 4-$(C_1-C_6)$alkoxy-$(C_1-C_6)$alkyl, and (h) when neither $X^1$, $X^2$ nor $X^3$ is a fluorinated alkoxy group, at least one of $R^1$, $R^3$, $R^4$, $R^5$, $R^6$, $R^7$ and $R^{13}$ is an aryl group substituted with a fluorinated alkoxy group;

pharmaceutically acceptable acid addition and base salts of compounds of the formula N.

For example (2S,3S)-2-phenyl-3-(2-trifluoromethoxybenzyl)]amino-piperidine—Compound 3; or a salt (e.g. hydrochloride) thereof; and (2S,3S)-3-(2-methoxy-5-trifluoromethoxybenzyl)amino-2-phenylpiperidine—Compound 6.

WO 93/01159, i.e. compounds of the formula (O) or a salt or prodrug thereof

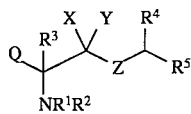

(O)

wherein

Q represents a group

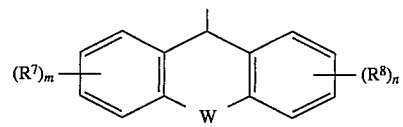

where W represents a bond, O, S, —$CH_2CH_2$—, —CH=CH— or a group $NR^6$, where $R^6$ is H or $C_{1-6}$alkyl and one or both of the phenyl rings may be replaced by a heteroaryl moiety;

X and Y each represent H or X and Y together form a group =O;

Z represents O, S or $NR^8$, where $R^8$ represents H or $C_{1-6}$alkyl;

$R^1$ and $R^2$ independently represent H; $C_{1-6}$alkyl optionally substituted by hydroxy, cyano, $COR^a$, $COOR^a$, $CONR^aR^b$, $COC_{1-4}alkylNR^aR^b$, $CONR^aC_{1-4}alkyl-CONR^aR^b$ or $NR^aR^b$, (where $R^a$ and $R^b$ each independently represent H, $C_{1-6}$alkyl, phenyl (optionally substituted by one or more of $C_{1-6}$alkyl, $C_{1-6}$alkoxy, halo and trifluoromethyl) or phenyl ($C_{1-4}$alkyl) (optionally substituted in the phenyl ring by one or more of $C_{1-6}$ alkyl, $C_{1-6}$ alkoxy, halo and trifluoromethyl)); phenyl($C_{1-4}$ alkyl), (optionally substituted by one or more of $C_{1-6}$alkyl, $C_{1-6}$ alkoxy, halo and trifluoromethyl in the phenyl ring); $C_{2-6}$alkylene; $COC_{1-6}$alkylhalo; $COR^a$; $COOR^a$; $CONHR^a$; $COC_{1-4}alkylNR^aR^b$; or $CONR^aC_{1-4}alkylCONR^aR^b$; (where $R^a$ and $R^b$ are as previously defined) or $R^1$ and $R^2$ together form a chain $(CH_2)_p$ where p is 4 or 5 and where one non-terminal methylene group may optionally be replaced by an oxygen atom or a group $NR^x$, where $R^x$ is H or $C_{1-6}$alkyl;

$R^3$ represents H or $C_{1-6}$alkyl;

$R^4$ represents H, $C_{1-6}$ alkyl or phenyl (optionally substituted by one or more of $C_{1-6}$ alkyl, $C_{2-6}$ alkenyl, $C_{2-6}$alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ each independently represent H, $C_{1-6}$alkyl, phenyl or trifluoromethyl);

$R^5$ represents $(CH_2)_q$phenyl, wherein q is 0, 1, 2 or 3 which may optionally be substituted in the phenyl ring by one or more of $C_{1-6}$ alkyl, $C_{2-6}$alkenyl, $C_{2-6}$alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ are as above defined;

each $R^7$ and $R^8$ independently represents $C_{1-6}$alkyl, $C_{2-6}$ alkenyl, $C_{2-6}$alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $COOR^c$ or $CONR^cR^d$ where $R^c$ and $R^d$ are as above defined; and m and n independently represent 0, 1, 2, 3 or 4.

WO 93/01160, i.e. compounds of the formula (P) or a salt or prodrug thereof

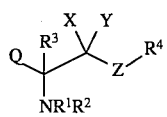

(P)

wherein Q represents $R^9CR^{10}R^{11}$ or $CH_2R^9CR^{10}R^{11}$ where $R^9$ is H or hydroxy and $R^{10}$ and $R^{11}$ each independently represent optionally substituted phenyl, optionally substituted benzyl, $C_{5-7}$cycloalkyl or ($C_{5-7}$cycloalkyl)methyl;

$R^1$ and $R^2$ independently represent H; $C_{1-6}$alkyl optionally substituted by hydroxy, cyano, $COR^a$, $COOR^a$, $CONR^aR^b$, $COC_{1-6}$alkyl$NR^aR^b$, $CONR^{12}C_{1-6}$alkyl$OR^a$, $CONR^{12}C_{1-6}$alkyl$CONR^aR^b$ or $NR^aR^b$ (where $R^a$ and $R^b$ each independently represent H, $C_{1-6}$ alkyl, phenyl (optionally substituted by one or more of $C_{1-6}$alkyl, $C_{1-6}$alkoxy, halo and trifluoromethyl), phenyl ($C_{1-4}$alkyl) (optionally substituted in the phenyl ring by one or more of $C_{1-6}$ alkyl, $C_{1-6}$alkoxy, halo and trifluoromethyl) or $R^a$ and $R^b$ together form a chain $(CH_2)_p$ optionally substituted by oxo where p is 4 or 5 and where one methylene group may optionally be replaced by an oxygen atom or a group $NR^x$, where $R^x$ is H or $C_{1-6}$alkyl, and $R^{12}$ represents H, $C_{1-6}$alkyl, phenyl (optionally substituted by one or more of $C_{1-6}$ alkyl, $C_{1-6}$alkoxy, halo and trifluoromethyl) or phenyl ($C_{1-4}$alkyl) (optionally substituted in the phenyl ring by one or more of $C_{1-6}$alkyl, $C_{1-6}$alkoxy, halo and trifluoromethyl); phenyl ($C_{1-4}$ alkyl) (optionally substituted by one or more of $C_{1-6}$ alkyl, $C_{1-6}$ alkoxy, halo and trifluoromethyl in the phenyl ring); $C_{2-6}$ alkenyl; $C_{2-6}$ alkynyl; $COR^a$; $COOR^a$; $COC_{1-6}$alkylhalo; $COC_{1-6}$alkyl$NR^aR^b$; $CONR^{12}C_{1-6}$alkyl$CONR^aR^b$; $CONR^aR^b$; or $SO_2R^a$; (where $R^a$, $R^b$ and $R^{12}$ are as previously defined) or $R^1$ and $R^2$ together form chain $(CH_2)_q$ optionally substituted by oxo where q is 4 or 5 and where one methylene group may optionally be replaced by an oxygen atom or a group $NR^x$, where $R^x$ is H or $C_{1-6}$ alkyl;

$R^3$ represents H, $C_{1-6}$ alkyl or $C_{2-6}$alkenyl;

$R^4$ represents $C_{1-3}$ alkyl substituted by a phenyl group which may itself optionally be substituted by one or more of $C_{1-6}$alkyl, $C_{2-6}$ alkenyl, $C_{2-6}$alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ and $CONR^cR^d$, where $R^c$ and $R^d$ independently represent H, $C_{1-6}$alkyl, phenyl or trifluoromethyl;

X and Y each represent H, or X and Y together represent a group =O; and

Z represents O, S or $NR^7$, where $R^7$ represents H or $C_{1-6}$ alkyl;

with the exception of

DL-diphenylalanine benzyl ester;

2-benzamido-3,3-diphenylpropanoyl benzamide; and 2-benzamido-3,4-diphenyl-butanoyl benzamide.

WO 93/01165; i.e. compounds of the formula (Q) or a salt or prodrug thereof

(Q)

wherein

Q represents optionally substituted phenyl, optionally substituted heteroaryl or optionally substituted naphthyl;

X and Y each represent H, $C_{1-6}$alkyl, $C_{2-6}$alkenyl or X and Y together form a group =O;

Z represents O or S;

$R^1$ represents H; $C_{1-6}$ alkyl optionally substituted by hydroxy, cyano, $COR^a$, $COOR^a$, $CONR^aR^b$, $COC_{1-4}$alkyl$NR^aR^b$, $CONR^aC_{1-4}$alkyl$CONR^aR^b$, (where $R^a$ and $R^b$ each independently represent H, $C_{1-6}$ alkyl, phenyl optionally substituted by one or more of $C_{1-6}$alkyl, $C_{1-6}$alkoxy, halo or trifluoromethyl or phenyl ($C_{1-4}$alkyl) optionally substituted in the phenyl ring by one or more of $C_{1-6}$ alkyl, $C_{1-6}$ alkoxy, halo or trifluoromethyl); phenyl($C_{1-4}$ alkyl), (optionally substituted in the phenyl ring by one or more of $C_{1-6}$ alkyl, $C_{1-6}$ alkoxy, halo or trifluoromethyl); $C_{2-6}$ alkylene; $COR^a$; $COOR^a$ $CONHR^a$; $COC_{1-6}$alkylhalo; $COC_{1-6}$alkyl$NR^aR^b$; or $CONR^aC_{1-6}$alkyl$CONR^aR^b$, where $R^a$ and $R^b$ are as previously defined;

$R^2$ represents $C_{1-6}$ alkyl substituted by hydroxy, cyano, $COR^a$, $COO R^a$, $CONR^aR^b$, $COC_{1-4}$alkyl$NR^aR^b$, $CONR^aC_{1-4}$alkyl$CONR^aR^b$ or $NR^aR^b$, (where $R^a$ and $R^b$ are as above defined); phenyl($C_{1-4}$-alkyl), (optionally substituted by one or more of $C_{1-6}$ alkyl, $C_{1-6}$ alkoxy, halo and trifluoromethyl in the phenyl ring); $C_{2-6}$ alkylene; $COR^a$; $COOR^a$; $CONHR^a$; $COC_{1-6}$alkylhalo; $COC_{1-6}$alkyl$NR^aR^b$; or $CONR^aC_{1-6}$alkyl$CONR^aR^b$, where $R^a$ and $R^b$ are as previously defined;

or $R^1$ and $R^2$ together form a chain $(CH_2)_p$ optionally substituted by oxo; where p is 4 or 5 and where one methylene group may optionally be replaced by an oxygen atom or a group $NR^x$, where $R^x$ is H or $C_{1-6}$ alkyl;

$R^3$ represents H or $C_{1-6}$alkyl;

$R^4$ represents H, $C_{1-6}$ alkyl or phenyl (optionally substituted by one or more of $C_{1-6}$ alkyl, $C_{2-6}$ alkenyl, $C_{2-6}$ alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ each independently represent H, $C_{1-6}$ alkyl, phenyl or trifluoromethyl); and $R^5$ represents $(CH_2)_q$phenyl, wherein q is 0, 1, 2 or 3, which may optionally be substituted in the phenyl ring by one or more of $C_{1-6}$ alkyl, $C_{2-6}$ alkenyl, $C_{2-6}$ alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ are as above defined.

WO 93/01169, i.e. compounds of the formula (R) or a salt or prodrug thereof

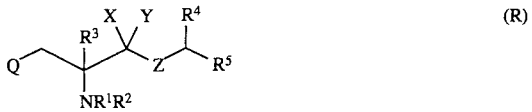

(R)

wherein q represents optionally substituted phenyl, optionally substituted naphthyl, optionally substituted indolyl, optionally substituted benzthiophenyl, optionally substituted benzofuranyl, optionally substituted benzyl or optionally substituted indazolyl;

z represents O, S or $NR^8$, where $R^8$ is H or $C_{1-6}$alkyl;

X and Y each represent H or X and Y together form a group =O;

$R^1$ and $R^2$ each independently represent H; $C_{1-6}$alkyl, optionally substituted by hydroxy, cyano, $COR^c$, $CO_2R^c$, $CONR^cR^d$, or $NR^cR^d$ (where $R^c$ and $R^d$ each independently represent H, $C_{1-12}$alkyl or phenyl optionally substituted by one or more of $C_{1-6}$alkyl, $C_{1-6}$alkoxy, halo or trifluoromethyl); phenyl($C_{1-4}$alkyl) (optionally substituted in the phenyl ring by one or more of $C_{1-6}$alkyl, $C_{1-6}$alkoxy, halo and trifluoromethyl); $COR^c$; $CO_2R^c$; $CONR^cR^d$; $CONR^cCOOR^d$; or $SO_2R^c$, where $R^c$ and $R^d$ are as above defined;

$R^3$ represents H or $C_{1-6}$alkyl; and

R⁴ represents H, $C_{1-6}$alkyl or phenyl (optionally substituted by 1, 2 or 3 groups selected from $C_{1-6}$alkyl, $C_{2-6}$alkenyl, $C_{2-6}$alkynyl, halo, cyano, nitro trifluoromethyl, trimethylsilyl, $OR^a$, $SR^a$, $SOR^a$, $NR^aR^b$, $NR^aCOR^b$, $NR^aCO_2R^b$; $CO_2R^a$ or $CONR^aR^b$, where $R^a$ and $R^b$ independently represent H, $C_{1-6}$alkyl, phenyl or trifluoromethyl); and R⁵ represents phenyl (optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ independently represent H, $C_{1-6}$alkyl, phenyl or trifluoromethyl); with the exception of benzyl 3-(3-indolyl)-2-amino propionate;
4-nitrobenzyl 3-(3-indolyl)-2-aminopropionate;
4-nitrobenzyl 2-(1,1-dimethylethoxycarbonylamino)-3-(3-indolyl)propionate;
benzyl 2-(1,1-dimethylethoxycarbonylamino)-3-(3-indolyl)propionate;
4-methoxybenzyl 2-(1,1-dimethylethoxycarbonylamino)-3-(3-indolyl)propionate;
2,4,6-trimethylbenzyl 3-(3-indolyl)-2-aminopropionate;
benzyl 3-(3-indolyl)-2 -((4-methylphylsulphonamido)propionate;
benzyl 2-(1,1-dimethylpropyloxycarbonylamino)-3-(3-indolyl)propionate;
4-nitrobenzyl 2-acetamido-3-(3-indolyl)propionate; benzyl 3-(1-naphthyl)-2-aminopropionate;
benzyl 3-(1-naphthyl)-2-(1,1-dimethylethoxycarbonyl amino)propionate;
benzyl 3-(2-naphthyl)-2-aminopropionate;
N-methyl-N-benzyl 3-(2-naphthyl)-2-(1,1-dimethylethoxycarbonylamino)propionamide;
N-methyl-N-(4-fluorobenzyl)-3-(2-naphthyl)-2-(1,1 -dimethylethoxycarbonylamino)propionamide;
N-methyl-N-(2-fluorobenzyl)-3-(2-naphthyl)-2-(1,1 -dimethylethoxycarbonylamino)propionamide;
N-methyl-N-benzyl-3-(1-naphthyl)-2-(1,1-dimethylethoxycarbonylamino)propionamide;
N-methyl-N-(4-fluorobenzyl)-3-(2-naphthyl)-2-aminopropionamide;
N-methyl-N-(3-fluorobenzyl)-3-(2-naphthyl)-2-aminopropionamide;
N-methyl-N-(3-fluorobenzyl)-3-(2-naphthyl)-2-aminopropionamide,
N-methyl-N-benzyl-3-(2-naphthyl)-2-aminopropionamide;
N-methyl-N-(3-fluorobenzyl)-3-(2-naphthyl)-2-(1,1 -dimethylethoxycarbonylamino)propionamide;
benzyl 3-phenyl-2-aminopropionate; and
4-nitrobenzyl 3-phenyl-2-aminopropionate.
WO 93/01170; i.e. compounds of the formula (S)

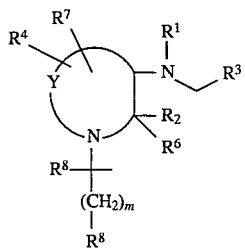

(S)

wherein Y is $(CH_2)_n$ wherein n is an integer from 1 to 6, and wherein any one of the carbon-carbon single bonds in said $(CH_2)_n$ may optionally be replaced by a carbon-carbon double bond, and wherein any one of the carbon atoms of said $(CH_2)_n$ may be optionally substituted with R⁴, and wherein any one of the carbon atoms of said $(CH_2)_n$ may optionally be substituted with R⁷;

m is an integer from 0 to 8, and any one of the carbon-carbon single bonds of $(CH_2)_m$ may optionally be replaced by a carbon-carbon double bond or a carbon-carbon triple bond, and any one of the carbon atoms of said $(CH_2)_m$ may be optionally substituted with R⁸, R¹ is hydrogen or $(C_1-C_8)$alkyl optionally substituted with hydroxy, alkoxy or fluoro;

R² is a radical selected from hydrogen, $(C_1-C_6)$ straight or branched alkyl, $(C_3-C_7)$cycloalkyl wherein one of the carbon atoms may optionally be replaced by nitrogen, oxygen or sulfur, aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl $(C_2-C_6)$alkyl, benzhydryl and benzyl, wherein each of said awl and heteroaryl groups and the phenyl moieties of said benzyl, phenyl $(C_2-C_6)$alkyl and benzhydryl may optionally be substituted with one or more substituents independently selected from halo, nitro, $(C_1-C_6)$alkyl, $(C_1-C_6)$alkoxy, trifluoromethyl, amino, $(C_1-C_6)$alkylamino, $(C_1-C_6)$alkyl-O—C(O)—, $(C_1-C_6)$alkyl-O—C(O)—, $(C_1-C_6)$alkyl, $(C_1-C_6)$alkyl-C(O)—O—, $(C_1-C_6)$alkyl-C(O)-$(C_1-C_6)$alkyl-O—, $(C_1-C_6)$alkyl-C(O)—, $(C_1-C_6)$alkyl-C(O)-$(C_1-C_6)$alkyl-, di-$(C_1-C_6)$alkylamino, —C(O)NH$(C_1-C_6)$alkyl, $(C_1-C_6)$alkyl-C(O)—NH-$(C_1-C_6)$alkyl, —NH(O)CH and —NH(O)$C_1-C_6$alkyl; and wherein one of the phenyl moieties of said benzhydryl may optionally be replaced by naphthyl, thienyl, furyl or pyridyl;

R⁵ is hydrogen, phenyl or $(C_1-C_6)$alkyl;

or R² and R⁵, together with the carbon to which they are attached, form a saturated carbocyclic ring having from 3 to 7 carbon atoms wherein one of said carbon atoms may optionally be replaced by oxygen, nitrogen or sulfur;

R³ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of said carbon atoms may optionally be replaced by nitrogen, oxygen or sulfur; wherein each of said aryl and heteroaryl groups may optionally be substituted with one or more substituents, and said $(C_3-C_7)$cycloalkyl may optionally be substituted with one or two substituents, each of said substituents being independently selected from halo, nitro, $(C_1-C_6)$alkyl, $(C_1-C_6)$alkoxy, trifluoromethyl, phenyl, amino, $(C_1-C_6)$alkylamino, —C(O)—NH-$(C_1-C_6)$alkyl, $(C_1-C_6)$alkyl-C(O)—NH-$(C_1-C_6)$alkyl, —NHC(O)H and —NHC(O)-$(C_1-C_6)$alkyl; and R⁴ and R⁷ are each independently selected from hydrogen, hydroxy, halo, amino, oxo (=O), nitrile, $(C_1-C_6)$alkylamino, di-$(C_1-C_6)$alkylamino, $(C_1-C_6)$alkoxy, $(C_1-C_6)$alkyl-O—C(O)—, $(C_1-C_6)$alkyl-O—C(O)-$(C_1-C_6)$alkyl, $(C_1-C_6)$alkyl-C(O)—O—, $(C_1-C_6)$alkyl-C(O)-$(C_1-C_6)$alkyl-O—, hydroxy-$(C_1-C_6)$alkyl, $(C_1-C_6)$alkoxy$(C_1-C_6)$alkyl, $(C_1-C_6)$alkyl-C(O)—, $(C_1-C_6)$alkyl-C(O)-$C_1-C_6)$alkyl- and the radicals set forth in the definition of R², R⁶ is NHC(O)R⁹, NHCH₂R⁹, SO₂R⁹ or one of the radicals set forth in any of the definitions of R², R⁴ and R⁷;

R⁸ is oximino (=NOH) or one of the radicals set forth in any of the definitions of R², R⁴ and R⁷;

$R^9$ is $(C_1-C_6)$alkyl, hydrogen, phenyl or phenyl $(C_1-C_6)$alkyl;

with the proviso that (a) when m is 0, $R^8$ is absent, (b) neither $R^4$, $R^6$, $R^7$ nor $R^8$ can form, together with the carbon to which it is attached, a ring with $R^5$, (c) when $R^4$ and $R^7$ are attached to the same carbon atom, then either each of $R^4$, and $R^7$ is independently selected from hydrogen, fluoro and $(C_1-C_6)$alkyl, or $R^4$ and $R^7$, together with the carbon to which they are attached, form a $(C_3-C_6)$ saturated carbocyclic ring that forms a spiro compound with the nitrogen-containing ring to which they are attached, (d) when n is 2 and either $R^4$ or $R^7$ is 5-hydroxy$(C_1-C_6)$alkyl or 5-$(C_1-C_6)$alkoxy-$(C_1-C_6)$alkyl, then the other of $R^4$ and $R^7$ is hydrogen, (e) when n is 2, neither $R^4$ nor $R^7$ is 4-hydroxy$(C_{1-6})$alkyl or 4-$(C_1-C_6)$alkoxy $(C_1-C_6)$alkyl, and (f) in all compounds of the formula (S), either $R^3$ is aryl substituted with at least one phenyl group, or one or both of $R^4$ and $R^7$ is hydroxy-$(C_1-C_6)$alkyl or $(C_1-C_6)$alkoxy$(C_1-C_6)$alkyl.

For example (2S,3S)-3-(5-carbomethoxy-2-methoxybenzyl)amino-2-phenylpiperidine hydrochloride—Compound 4;

Preferred tachykinin antagonists for use in the present invention include those compounds generically and specifically disclosed in EP 522808, WO 92/17449, WO 93/00331, WO 93/01170 and EP528495.

The tachykinin antagonists may be administered as the raw chemical but the active ingredients are preferably presented as a pharmaceutical formulation. Suitable pharmaceutical formulations are described in the above referenced patent specifications.

Thus, the tachykinin antagonists may be formulated for oral, buccal, parenteral, depot or rectal administration or in a form suitable for administration by inhalation or insufflation (either through the mouth or nose). Oral and parenteral formulations are preferred.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or lozenges formulated in conventional manner.

The tachykinin antagonists may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The tachykinin antagonists may also be formulated in rectal compositions such as suppositories or retention enemas, e.g. containing conventional suppository bases such as cocoa butter or other glycerides.

The tachykinin antagonists may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the tachykinin antagonists may be formulated as solutions for administration via a suitable metered or unit dose device or alternatively as a powder mix with a suitable carrier for administration using a suitable delivery device.

Suitable dose ranges are also described in the above referenced patent specifications, that is to say that for use as anti-emetics the compounds may be used at doses appropriate for other conditions for which tachykinin antagonists are known to be useful. It will be appreciated that it may be necessary to make routine variations to the dosage, depending on the age and condition of the patient, and the precise dosage will be ultimately at the discretion of the attendant physician or veterinarian. The dosage will also depend on the route of administration and the particular compound selected. A suitable dose range is for example 0.1 mg/kg to about 400mg/kg bodyweight per day.

The tachykinin antagonists may, if desired, be administered in combination with one or more other therapeutic agents and formulated for administration by any convenient route in a conventional manner. Appropriate doses will be readily appreciated by those skilled in the art. For example, the tachykinin antagonists may be administered in combination with a systemic anti-inflammatory corticosteroid such as methyl prednisolone or dexamethasone, or a $5HT_3$ antagonist such as ondansetron, granisetron or metoclopramide.

Biological Data

The anti-emetic activity of the test compounds 1, 2 (as hydrochloride salt), 3, 4 and 5 (as racemates) and 6 (as single enantiomer) defined hereinbefore was demonstrated by their ability to inhibit cisplatin- or radiation-induced emesis in the ferret.

Cisplatin Test

In this model of emesis the onset of retching and vomiting occurs approximately 1 hour after the administration of cisplatin (200 mg/m² i.p.). At first retch in response to cisplatin, the test compound was administered (e.g. i.p., p.o., i.v., s.c., i.c.v.) and its effect on emesis determined by comparison with appropriate controls (e.g. water).

Radiation Test

In this model of emesis the onset of retching and vomiting occurs approximately 20 minutes after whole body irradiation (2 Grey≡200 Rads). The test compound is administered (e.g. i.p., p.o., i.v., s.c.) immediately after irradiation and its effect on emesis determined by comparison with appropriate controls. In the case of compound 6, this test compound was administered 90 minutes before whole body irradiation.

Test compounds 1 to 6 inhibited emesis in the above tests at the doses shown:

| Compound | Dose mg/kg | Test |
|---|---|---|
| 1 | 10 (i.p.) | cisplatin |
| 2 | 1.0 (s.c.) | radiation |
| 3 | 10 (s.c.) | cisplatin |
| 4 | 10 (s.c.) | cisplatin |
| 5 | 10 (s.c) | cisplatin |
| 6 | 0.03 (s.c) | radiation |

Reference Example

The compound (2S,3S)-3-(2-methoxybenzylamino)-2-phenyl piperidine inhibited cisplatin-induced emesis in the ferret when administered at a dose of 3 mg/kg i.p. The (2R,3R) enantiomer of the above compound, which is 1000-fold less active as an $NK_1$ receptor antagonist than the (2S,3S) enantiomer, was inactive in the cisplatin emesis test at the same dose.

We claim:

1. A method for the treatment or prophylaxis of emesis of a mammal, comprising administering to said mammal an effective amount of an $NK_1$ receptor antagonist of formula J, N, S or G:

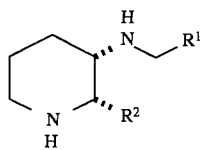
(J)

wherein $R^1$ is aryl selected from the group consisting of indanyl, phenyl and naphthyl; heteroaryl selected from the group consisting of thienyl, furyl, pyridyl and quinolyl; or cycloalkyl having 3 to 7 carbon atoms, wherein one of said carbon atoms may optionally be replaced by nitrogen, oxygen or sulfur; wherein each of said aryl and heteroaryl groups may optionally be substituted with one or more substituents, and said $(C_3-C_7)$cycloalkyl may optionally be substituted with one or two substituents, said substituents being independently selected from the group consisting of chloro, fluoro, bromo, iodo, nitro, $(C_1-C_{10})$alkyl optionally substituted with from one to three fluoro groups, $(C_1-C_{10})$alkoxy optionally substituted with from one to three fluoro groups, amino, $(C_1-C_{10})$alkyl-S—, $(C_1-C_{10})$alkyl-S(O)—, $(C_1-C_{10})$alkyl-$SO_2$—, phenyl, phenoxy, $(C_1-C_{10})$alkyl-$SO_2$NH—, $(C_1-C_{10})$alkyl-$SO_2$NH-$(C_1-C_{10})$alkyl-, $(C_1-C_{10})$alkylamino-di$(C_1-C_{10})$alkyl-, cyano, hydroxy, cycloalkoxy having 3 to 7 carbon atoms, $(C_1-C_6)$alkylamino, $(C_1-C_6)$dialkylamino, HC(O)NH— and $(C_1-C_{10})$alkyl-C(O)—NH—, wherein the nitrogen atoms of said amino and $(C_1-C_6)$alkylamino groups may optionally be protected with an appropriate protecting group; and $R^2$ is thienyl, benzhydryl, naphthyl or phenyl optionally substituted with from one to three substituents independently selected from the group consisting of chloro, bromo, fluoro, iodo, cycloalkoxy having 3 to 7 carbon atoms, $(C_1-C_{10})$alkyl optionally substituted with from one to three fluoro groups, and $(C_1-C_{10})$alkoxy optionally substituted with from one to three fluoro groups;

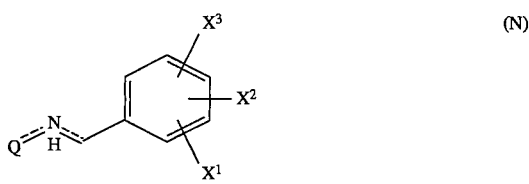
(N)

wherein $X^1$ is hydrogen, $(C_1-C_{10})$alkoxy optionally substituted with from one to three fluorine atoms or $(C_1-C_{10})$alkyl optionally substituted with from one to three fluorine atoms;

$X^2$ and $X^3$ are independently selected from the group consisting of hydrogen, halo, nitro, $(C_1-C_{10})$alkyl optionally substituted with from one to three fluorine atoms, $(C_1-C_{10})$alkoxy optionally substituted with form one to three fluorine atoms, trifluoromethyl, hydroxy, phenyl, cyano, amino, $(C_1-C_6)$-alkylamino, di-$(C_1-C_6)$alkylamino, —C(O)—NH-$(C_1-C_6)$-alkyl, $(C_1-C_6)$alkyl-C(O)—NH-$(C_1-C_6)$alkyl, hydroxy, $(C_1-C_4)$alkyl, $(C_1-C_4)$alkyoxy$(C_1-C_4)$alkyl, —NH-C(O)H and —NHC(O)-$(C_1-C_6)$alkyl; and Q is a group of the formula

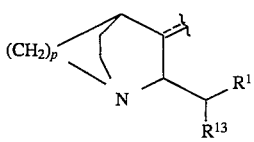
II

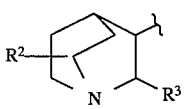
III

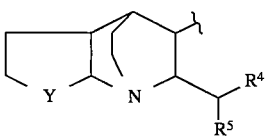
IV

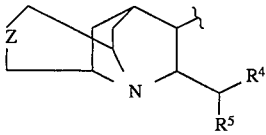
V

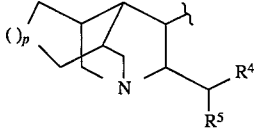
VI

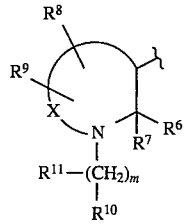
VII

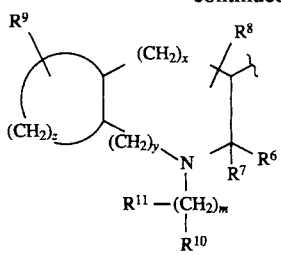

wherein $R^1$ is a radical selected from the group consisting of furyl, thienyl, pyridyl, indolyl, biphenyl and phenyl optionally substituted with one or two substituents independently selected from the group consisting of halo, $(C_1-C_{10})$alkyl optionally substituted with from one to three fluorine atoms, $(C_1-C_{10})$alkoxy optionally substituted with from one to three fluorine atoms, carboxy, benzyloxycarbonyl and $(C_1-C_3)$alkoxy-carbonyl;

$R^{13}$ is selected from the group consisting of $(C_3-C_{44})$ branched alkyl, $(C_5-C_6)$ branched alkenyl, $(C_5-C_7)$cycloalkyl, and the radicals named in the definition of $R^1$;

$R^2$ is hydrogen or $(C_1-C_6)$alkyl;

$R^3$ is phenyl, biphenyl, naphthyl, pyridyl, benzhydryl, thienyl or furyl, and $R^3$ may optionally be substituted with from one to three substituents independently selected from the group consisting of halo, $(C_1-C_{10})$alkyl optionally substituted with from one to three fluorine atoms and $(C_1-C_{10})$alkoxy optionally substituted with from one to three fluorine atoms;

Y is $(CH_2)_l$ wherein l is an integer from one to three or Y is a group of the formula

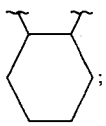

Z is oxygen, sulfur, amino, $(C_1-C_3)$alkylamino or $(CH_2)_n$ wherein n is zero, one or two;

o is two or three;

p is zero or one;

$R^4$ is furyl, thienyl, pyridyl, indolyl, biphenyl, or phenyl optionally substituted with one or two substituents independently selected from the group consisting of halo, $(C_1-C_{10})$alkyl optionally substituted with from one to three fluorine atoms, $(C_1-C_{10})$alkoxy optionally substituted with from one to three fluorine atoms, carboxy, $(C_1-C_3)$alkoxycarbonyl and benzyloxycarbonyl;

$R^5$ is thienyl, biphenyl or phenyl optionally substituted with one or two substituents independently selected from the group consisting of halo, $(C_1-C_{10})$alkyl optionally substituted with from one to three fluorine atoms and $(C_1-C_{10})$alkoxy optionally substituted with from one to three fluorine atoms;

each of the two dashed lines in formula (N) and the dashed line in formula (II) represents an optional double bond that may optionally exist when Q is a group of the formula (II);

X is $(CH_2)_q$ wherein q is an integer from 1 to 6, and wherein any one of the carbon-carbon single bonds in said $(CH_2)_q$ may optionally be replaced by a carbon-carbon double bond, and wherein any one of the carbon atoms of said $(CH_2)_q$ may optionally be substituted with $R^8$, and wherein any one of the carbon atoms of said $(CH_2)_q$ may be substituted with $R^9$;

m is an integer from 0 to 8, and any one of the carbon-carbon single bonds of $(CH_2)_m$ may optionally be replaced by a carbon-carbon double bond, or a carbon-carbon triple bond, and any one of the carbon atoms of said $(CH_2)_m$ may optionally be substituted with $R^{11}$;

$R^6$ is a radical selected from the group consisting of hydrogen, $(C_1-C_6)$ straight or branched alkyl, $(C_3-C_7)$cycloalkyl wherein one of the carbon atoms may optionally be replaced by nitrogen, oxygen or sulfur; aryl selected from the group consisting of biphenyl, phenyl, indanyl and naphthyl; heteroaryl selected from the group consisting of thienyl, furyl, pyridyl, thiazolyl, isothiazolyl, oxazolyl, isoxazolyl, triazolyl, tetrazolyl and quinolyl; phenyl$(C_2-C_6)$alkyl, benzhydryl and benzyl, wherein each of said aryl and heteroaryl groups and the phenyl moieties of said benzyl, phenyl$(C_2-C_6)$alkyl and benzhydryl may optionally be substituted with one or more substituents independently selected from the group consisting of halo, nitro, $(C_1-C_{10})$alkyl optionally substituted with from one to three fluorine atoms, $(C_1-C_{10})$alkoxy optionally substituted with from one to three fluorine atoms, amino, hydroxy-$(C_1-C_6)$alkyl, $(C_1-C_6)$alkoxy-$(C_1-C_6)$alkyl, $(C_1-C_6)$alkylamino, $(C_1-C_6)$alkyl-O—C(O)—, $(C_1-C_6)$alkyl-O—C(O)—C-$(C_1-C_6)$alkyl, $(C_1-C_6)$alkyl-C—(O)—(O)—, $(C_1-C_6)$alkyl-C(O)$(C_1-C_6)$alkyl-O—, $(C_1-C_6)$alkyl-C(O), $(C_1-C_6)$alkyl-C(O)$(C_1-C_6)$alkyl-, di-$(C_1-C_6)$alkylamino, —C(O)NH-$(C_1-C_6)$-alkyl-, $(C_1-C_6)$alkyl-C(O)—NH-$(C_1-C_6)$alkyl, —NHC(O)H and NHC(O)-$(C_1-C_6)$alkyl; and wherein one of the phenyl moieties of said benzhydryl may optionally be replaced by naphthyl, thienyl, furyl or pyridyl;

$R^7$ is hydrogen, phenyl or $(C_1-C_6)$alkyl;

or $R^6$ and $R^7$, together with the carbon to which they are attached, form a saturated carbocyclic ring having from 3 to 7 carbon atoms wherein one of said carbon atoms may optionally be replaced by oxygen, nitrogen or sulfur;

$R^8$ and $R^9$ are each independently selected from the group consisting of hydrogen, hydroxy, halo, amino, oxo (=O), nitrile, hydroxy-$(C_1-C_6)$alkyl, $(C_1-C_6)$-alkoxy-$(C_1-C_6)$alkyl, $(C_1-C_6)$alkylamino, di-$(C_1-C_6)$alkylamino, $(C_1-C_6)$alkoxy, $(C_1-C_6)$alkyl-O—C(O)—, $(C_1-C_6)$-alkyl-O—C(O)-$(C_1-C_6)$alkyl, $(C_1-C_6)$alkyl-C(O)—O, $(C_1-C_6)$alkyl-C(O)-$(C_1-C_6)$alkyl-O—, $(C_1-C_6)$alkyl-C(O)—, $(C_1-C_6)$alkyl-C(O)-$(C_1-C_6)$alkyl-, and the radicals set forth in the definition of $R^6$;

$R^{10}$ is NHCR$^{12}$, NHCH$_2$R$^{12}$, NHSO$_2$R$^{12}$, or one of the radicals set forth in any of the definitions of $R^6$, $R^8$ and $R^9$;

$R^{11}$ is oximino (=NOH) or one of the radicals set forth in any of the definitions of $R^6$, $R^8$ and $R^9$; and $R^{12}$ is $(C_1-C_6)$alkyl, hydrogen, phenyl$(C_1-C_6)$alkyl or phenyl optionally substituted with $(C_1-C_6)$alkyl, and with the provisos that (a) when m is O, $R^{11}$ is absent;

(b) neither $R^8$, $R^9$, $R^{10}$ nor $R^{11}$ can form, together with the carbon to which it is attached, a ring with $R^7$;

(c) when Q is a group of the formula (VIII), $R^8$ and $R^9$ cannot be attached to the same carbon atom;

(d) when $R^8$ and $R^9$ are attached to the same carbon atom, then either each of $R^8$ and $R^9$ is independently selected from hydrogen, fluoro, $(C_1-C_6)$alkyl, hydroxy-$(C_1-C_6)$alkyl and $(C_1-C_6)$alkoxy-$(C_1-C_6)$alkyl, or $R^8$ and $R^9$, together with the carbon to which they are attached, form a $(C_3-C_{46})$ saturated carbocyclic ring that forms a spiro compound with the nitrogen-containing ring to which they are attached;

(e) the nitrogen of formula (N) cannot be double bonded to both Q and the substituted benzyl group to which it is attached;

(f) when Q is a group of the formula (VII) and q is 2 and either $R^8$ or $R^9$ is 5-hydroxy-$(C_1-C_6)$alkyl or 5-$(C_1C_6)$alkoxy-$(C_1-C_6)$alkyl, then the other of $R^8$ or $R^9$ is either 5-$(C_1-C_6)$alkyl or hydrogen;

(g) when Q is a group of the formula (VII) and q is 2, then neither $R^8$ nor $R^9$ is 4-hydroxy-$(C_1-C_6)$alkyl or 4-$(C_1-C_6)$alkoxy-$(C_1-C_6)$alkyl; and (h) when neither $X^1$, $X^2$ nor $X^3$ is a fluorinated alkoxy group, at least one of $R^1$, $R^3$, $R^4$, $R^5$, $R^6$, $R^7$ and $R^{13}$ is an aryl group substituted with a fluorinated alkoxy group;

and pharmaceutically acceptable acid addition and base salts of compounds of the formula (N);

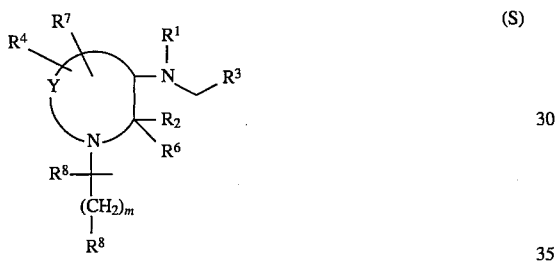

(S)

wherein

Y is $(CH_2)_n$ wherein n is an integer from 1 to 6, and wherein any one of the carbon-carbon single bonds in said $(CH_2)_n$ may optionally be replaced by a carbon-carbon double bond, and wherein any one of the carbon atoms of said $(CH_2)_n$ may optionally be substituted with $R^4$, and wherein any one of the carbon atoms of said $(CH_2)_n$ may be substituted with $R^7$;

m is an integer from 0 to 8, and any one of the carbon-carbon single bonds of $(CH_2)_m$ may optionally be replaced by a carbon-carbon double bond, or a carbon-carbon triple bond, and any one of the carbon atoms of said $(CH_2)_m$ may be optionally substituted with $R^8$;

$R^1$ is hydrogen or $(C_1-C_8)$alkyl optionally substituted with hydroxy, alkoxy or fluoro;

$R^2$ is a radical selected from the group consisting of hydrogen, $(C_1-C_6)$ straight or branched alkyl, $(C_3-C_{47})$cycloalkyl wherein one of the carbon atoms may optionally be replaced by nitrogen, oxygen or sulfur; aryl selected from the group consisting of phenyl and naphthyl; heteroaryl selected from the group consisting of indanyl, thienyl, furyl, pyridyl, thiazolyl, isothiazolyl, oxazolyl, triazolyl, tetrazolyl and quinolyl; phenyl$(C_2-C_6)$alkyl, benzhydryl and benzyl, wherein each of said aryl and heteroaryl groups and the phenyl moieties of said benzyl, phenyl$(C_2-C_6)$alkyl and benzhydryl may optionally be substituted with one or more substituents independently selected from halo, nitro, $(C_1-C_6)$alkyl, $(C_1-C_6)$alkoxy, trifluoromethyl, amino, $(C_1-C_6)$alkylamino, $(C_1-C_6)$alkyl-O—C(O)—, $(C_1-C_6)$alkyl-O—C(O)-$(C_1-C_6)$alkyl, $(C_1-C_6)$alkyl-C(O)—O, $(C_1-C_6)$alkyl-C(O)-$(C_1-C_6)$alkyl-O—, $(C_1-C_6)$alkyl-O—, $(C_1-C_6)$alkyl-C(O)—, $(C_1-C_6)$alkyl-C(O)-$(C_1-C_6)$alkyl-, di-$(C_1-C_6)$alkyl-amino, —C(O)NH-$(C_1-C_6)$alkyl-, $(C_1-C_6)$alkyl-C(O)—NH-$(C_1-C_6)$alkyl, —NH(O)CH and —NH(O)C-$(C_1-C_6)$alkyl; and wherein one of the phenyl moieties of said benzhydryl may optionally be replaced by naphthyl, thienyl, furyl or pyridyl;

$R^5$ is hydrogen, phenyl or $(C_1-C_6)$alkyl;

or $R^2$ and $R^5$, together with the carbon to which they are attached, form a saturated carbocyclic ring having from 3 to 7 carbon atoms wherein one of said carbon atoms may optionally be replaced by oxygen, nitrogen or sulfur;

$R^3$ is aryl selected from the group consisting of phenyl and naphthyl; heteroaryl selected from the group consisting of indanyl, thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of said carbon atoms may optionally be replaced by nitrogen, oxygen or sulfur; wherein each of said aryl and heteroaryl groups may optionally be substituted with one or more substituents, and said $(C_3-C_7)$cycloalkyl may optionally be substituted with one or two substituents, each of said substituents being independently selected from the group consisting of halo, nitro, $(C_1-C_6)$alkyl, $(C_1-C_6)$alkoxy, trifluoromethyl, phenyl, amino, $(C_1-C_6)$alkylamino, —C(O)NH-$(C_1-C_6)$alkyl, $(C_1-C_6)$alkyl C(O)—NH-$(C_1-C_6)$alkyl, —NHC(O)H and —NHC(O)-$(C_1-C_6)$alkyl;

$R^4$ and $R^7$ are each independently selected from the group consisting of hydrogen, hydroxy, halo, amino, oxo (=O), nitrile, $(C_1-C_6)$alkylamino, di-$(C_1-C_6)$alkylamino, $(C_1-C_6)$alkoxy, $(C_1-C_6)$alkyl-O—C(O)—, $(C_1-C_6)$alkyl-O—C(O)-$(C_1-C_6)$alkyl, $(C_1-C_6)$alkyl-C(O)—O, $(C_1-C_6)$alkyl-C(O)-$(C_1-C_6)$alkyl-O, hydroxy-$(C_1-C_6)$alkyl, $(C_1-C_6)$alkoxy$(C_1-C_6)$alkyl, $(C_1-C_6)$alkyl-C(O)—, $(C_1-C_6)$alkyl-C(O)-$(C_1-C_6)$alkyl- and the radicals set forth in the definition of $R^2$;

$R^6$ is $NHC(O)R^9$, $NHCH_2R^9$, $SO_2R^9$, or one of the radicals set forth in any of the definitions of $R^2$, $R^4$ and $R^7$;

$R^8$ is oximino (=NOH) or one of the radicals set forth in any of the definitions of $R^2$, $R^4$ and $R^7$;

$R^9$ is $(C_1-C_6)$alkyl, hydrogen, phenyl or phenyl$(C_1-C_6)$alkyl;

with the provisos that (a) when m is O, $R^8$ is absent;

(b) neither $R^4$, $R^6$, $R^7$ nor $R^8$ can form, together with the carbon to which it is attached, a ring with $R^5$;

(c) when $R^4$ and $R^7$ are attached to the same carbon atom, then either each of $R^4$ and $R^7$ is independently hydrogen, fluoro or $(C_1-C_6)$alkyl, or $R^1$ and $R^7$, together with the carbon to which they are attached, form a $(C_3-C_6)$ saturated carbocyclic ring that forms a spiro compound with the nitrogen-containing ring to which they are attached;

(d) when n is 2 and either $R^4$ or $R^7$ is 5-hydroxy$(C_1-C_6)$alkyl or 5-$(C_1-C_6)$alkoxy-$(C_1-C_6)$alkyl, then the other of $R^4$ and $R^7$ is hydrogen;

(e) when n is 2, neither $R^4$ nor $R^7$ is 4-hydroxy$(C_1-C_6)$alkyl or 4-$(C_1-C_6)$alkoxy$(C_1-C_6)$alkyl; and (f) in all compounds of the formula (S), either $R^3$ is aryl substituted with at least one phenyl group, or one or both of $R^4$ and $R^7$ is hydroxy-$(C_1-C_6)$alkyl or $(C_1-C_6)$alkoxy$(C_1-C_6)$alkyl;

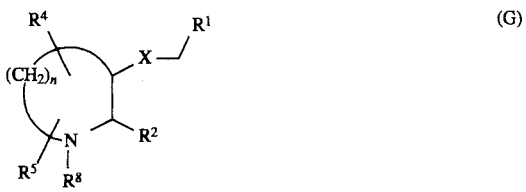

wherein n is 1, 2 or 3 and where any carbon atom of $(CH_2)_n$ may be substituted by $R^4$ and/or $R^5$;

X represents O or S;

$R^1$ represents phenyl optionally substituted by 1, 2 or 3 groups selected from the group consisting of $C_{1-6}$alkyl, $C_{2-6}$alkenyl; $C_{2-6}$alkynyl, halo, cyano, nitro, trifluoromethyl, trimethylsilyl, —$OR^a$, $SR^a$, $SOR^a$, $SO_2R^a$, —$NR^aR^b$, —$NR^aCOR^b$, —$NR^aCO_2R^b$, $CO_2R^a$, or —$CONR^aR^b$;

$R^2$ represents aryl selected from the group consisting of phenyl and naphthyl; heteroaryl selected from the group consisting of indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, halo or trifluoromethyl;

$R^4$ and $R^5$ each independently represent H, halo, $CH_2OR^9$, $C_{1-6}$alkyl, oxo, $CO_2R^{10}$ or $CONR^{10}R^{11}$;

$R^8$ represents H, $COR^9$, $CO_2R^{10}$, $COCONR^{10}R^{11}$, $COCO_2R^{10}$ or $C_{1-6}$alkyl optionally substituted by a group selected from the group consisting of $CO_2R^{10}$, $CONR^{10}R^{11}$, hydroxy, cyano, $COR^9$, $NR^{10}R^{11}$, $C(NOH)NR^{10}R^{11}$, CONHphenyl-$(C_{1-4}$alkyl), $COCO_2R^{10}$, $COCONR^{10}R^{11}$ and phenyl optionally substituted by one or more substituents selected from the group consisting of $C_{1-6}$alkyl, $C_{1-6}$alkoxy, halo and trifluoromethyl;

$R^a$ and $R^b$ each independently represent H, $C_{1-6}$alkyl, phenyl or trifluoromethyl;

$R^9$ represents H, $C_{1-6}$alkyl or phenyl; and $R^{10}$ and $R^{11}$ each independently represent H or $C_{1-6}$alkyl.

2. A method according to claim 1 wherein said emesis is induced by cancer chemotherapeutic agents, radiation sickness, radiation therapy, poisons, toxins, pregnancy, vestibular disorders, post-operative sickness, gastrointestinal obstruction, reduced gastrointestinal motility, visceral pain, migraine, increased intercranial pressure, decreased intercranial pressure, or opioid analgesics.

3. A method according to claim 2 wherein said emesis is induced by a cancer chemotherapeutic agent, radiation sickness or radiation therapy.

4. A method as claimed in claim 3 wherein the $NK_1$ receptor antagonist is administered to said mammal prior to administration of a cancer chemotherapeutic agent.

5. A method as claimed in claim 4 wherein the cancer chemotherapeutic agent is selected from the group consisting of cyclophosphamide, carmustine, lomustine, chloroambucil, dactinomycin, doxorubicin, mitomycin-C, bleomycin, cytarabine, methotrexate, 5-fluoroacil, etoposide, vinblastine, vincristine, cisplatin, decarbazine, procarbazine, hydroxyurea, and combinations thereof.

6. A method as claimed in claim 5 wherein the cancer chemotherapeutic agent is cisplatin.

7. A method as claimed n claim 5 wherein the cancer chemotherapeutic agent is cyclophosphamide.

8. A method as claimed in claim 3 wherein the $NK_1$ receptor antagonist is administered to the mammal prior to radiation therapy.

9. A method according to claim 3 wherein said cancer chemotherapeutic agent is selected from the group consisting of from cyclophosphamide, carmustine, lomustine, chloroambucil, dactinomycin, doxoruibicin, mitomycin-C, bleomycin, cytarabine, methotrexate, 5-fluorouracil, etoposide, vinblastine, vincristine, cisplatin, decarbazine, procarbazine, hydroxyurea, and combinations thereof.

10. A method according to claim 9 wherein said emesis is induced by cisplatin.

11. A method according to claim 9 wherein said emesis is induced by cyclophosphamide.

12. A method according to claim 1 wherein the tachykinin antagonist is a compound selected from:

2-ammonium-1-((3,5-bis(trifluoromethyl)phenyl) methyloxy)-3,3-diphenylpropane;

(2S,3S)-3-(2-methoxy-5-methylmercaptobenzylamino)-2-phenylpiperidine;

(2S,3S)-2-phenyl-3-(2-trifluoromethoxybenzyl)]aminopiperidine;

(2S,3S)-3-(5-carbomethoxy-2-methoxybenzyl)amino-2-phenylpiperidine;

cis-3-((3,5-dimethylphenyl)methyloxy)-2-phenylpiperidine; or a pharmaceutically acceptable salt thereof.

13. A method according to claim 1 wherein the tachykinin antagonist is (2S,3S)-3-(2-methoxy-5-trifluoromethoxybenzyl)amino-2-phenylpiperidine or a pharmaceutically acceptable salt thereof.

* * * * *